United States Patent
Ramazanova et al.

(10) Patent No.: US 7,157,592 B1
(45) Date of Patent: Jan. 2, 2007

(54) METHOD FOR PRODUCING ORGANO-METALLIC COMPOUNDS OF CYCLOPENTADIENE

(75) Inventors: Elmira M. Ramazanova, Baku (AZ); Alimamed L. Shebanov, Baku (AZ)

(73) Assignee: Property Development Corporation International Ltd., Inc., Baku (AZ)

( * ) Notice: Subject to any disclaimer, the term of this patent is extended or adjusted under 35 U.S.C. 154(b) by 0 days.

(21) Appl. No.: 11/322,929

(22) Filed: Dec. 30, 2005

(51) Int. Cl.
  *C07F 17/00* (2006.01)
  *C07F 15/00* (2006.01)
  *C07F 7/00* (2006.01)
(52) U.S. Cl. .......... 556/143; 556/43; 556/46; 556/53; 556/58; 556/136
(58) Field of Classification Search .......... 556/43, 556/46, 53, 58, 136, 143
See application file for complete search history.

(56) References Cited

U.S. PATENT DOCUMENTS

| | | | |
|---|---|---|---|
| 2,763,700 A | | 9/1956 | Hobbs |
| 3,063,974 A | | 11/1962 | Pruett et al. |
| 3,071,605 A | * | 1/1963 | Morehouse ............ 556/53 |
| 3,122,577 A | * | 2/1964 | Lindstrom et al. ........ 556/143 |
| 3,217,022 A | | 11/1965 | Cordes |
| 3,259,642 A | * | 7/1966 | Schenck et al. ........... 556/7 |
| 3,285,946 A | | 11/1966 | De Witt et al. |
| 3,382,268 A | * | 5/1968 | Cais .................... 556/143 |
| 5,670,681 A | | 9/1997 | Kuber et al. |
| 6,124,488 A | | 9/2000 | Gruter et al. |
| 6,162,937 A | | 12/2000 | Dang et al. |
| 2002/0161253 A1 | * | 10/2002 | Voll et al. ............... 556/143 |

FOREIGN PATENT DOCUMENTS

| | | |
|---|---|---|
| GB | 733129 | 7/1955 |
| GB | 744450 | 2/1956 |
| GB | 737110 | 12/1956 |

OTHER PUBLICATIONS

Wilkinson G., Pauson P.L., Cotton F.A. J. Am. Chem. Soc. vol. 76, p. 1970 (1954).
Wilkinson G., Cotton F.A., Birmingham J.M. J. Inorg. and Nuclear Chem., vol. 2, p. 95, (1956).
Wilkinson G., Birmingham J.M. J. Am. Chem. Soc. vol. 76, p. 4281 (1954).
Wilkinson G., Birmingham J.M. J. Am. Chem. Soc. vol. 76, p. 6210 (1954).
Wilkinson G., Cotton F.A., Chemistry and Industry, Mar. 13, 1954, p. 307.
Unknown Author, Collection 8, Moscow, 1958, pp. 64-68, English abstract and Russian article attached as one document.
Fischer E.O. Jira R.Z. Naturforsch, vol. 86, p. 327 (1953) English abstract and German article attached as one document.
Fischer E.O. Jira R.Z. Naturforsch, vol. 86, p. 217 (1953) English abstract and German article attached as one document.
Fischer E.O. Hafner W.Z. Stahl H.O.Z. Inorganic Chem., vol. 282, p. 47 (1955) [No copy presently available].
Wilkinson G., Org. syntheses. vol. 36, p. 31 (1956) [No copy presently available].

* cited by examiner

*Primary Examiner*—Porfirio Nazario-Gonzalez
(74) *Attorney, Agent, or Firm*—Colter Jennings

(57) ABSTRACT

A method for producing ferrocene and other organometallic compounds of cyclopentadiene is disclosed. Dry iron chloride (or other selected metal salt) is added to a solution of cyclopentadiene, diethylamine, potassium and dibenzo-18-crown-6 ether in a cooled flask under a dry nitrogen atmosphere. The solution is mixed vigorously for a few hours and any excess diethylamine is evaporated. Ferrocene (or other organometallic compounds of cyclopentadiene) is extracted from the residue using petroleum ether, and any solvent is removed.

9 Claims, No Drawings

METHOD FOR PRODUCING ORGANO-METALLIC COMPOUNDS OF CYCLOPENTADIENE

BACKGROUND

This invention relates to the production of cyclopentadiene metal compounds, such as those of iron, titanium, zirconium, hafnium, vanadium, chromium, molybdenum, tungsten, manganese, iron, ruthenium, osmium, cobalt, rhodium, or nickel and in particular to a process for the production of ferrocene from a mixture of $FeCl_2$, cyclopentadiene, diethylamine, and dibenzo-18-crown-6-potassium complex followed by petroleum ether extraction.

Ferrocene (bis-cyclopentadieneyl iron, with the chemical formula $Fe(C_5H_5)_2$) is an organometallic compound having the structure:

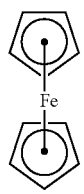

(I)

Ferrocene has numerous uses, including use as a gasoline antiknock additive (in place of tetraethyl lead), in ammonia synthesis reactions, and in fertilizer production. As a fuel catalyst for rocket propellants, ferrocene may improve combustion speed and lower the temperature of exhaust pipes. When added to fuel oils, ferrocene can help reduce smoke and air pollution, increase power and increase fuel economy. Ferrocene also has application in such diverse areas as integrated circuit manufacture, plastics stabilization, photography and printing, and biochemistry and medicine.

Prior processes for producing ferrocene have not typically been economically viable. For instance, one prior process (see U.S. Pat. No. 3,217,022) involves dissolving ferric chloride in methanol and adding iron powder. Sodium methylate and then cyclopentadiene are added, and ferrocene ultimately precipitates out of the solution. Unfortunately, this method involves large amounts of methanol, difficult purification steps to remove by-products of the process, and only results in reported yields of 65–70%.

Another method, described at http://www.orgsyn.org/orgsyn/orgsyn/prepContent.asp?prep=cv4p0473, mixes cyclopentadiene with iron chloride, diethylamine, and tetrahydroamine. This method takes several hours of vigorous stirring. This method also involves large amounts of solvent and significant and difficult preparatory treatments, such as peroxide removal and drying.

Still another prior process involves a two step process using tetrahydrofuran to form ferric chloride, $FeCl_2$, followed by reaction of the $FeCl_2$ with sodium cyclopentadiene under a nitrogen atmosphere. Ferrocene is then extracted using petroleum ether. This process typically takes several hours, and requires use of sodium and tetrahydrofuran.

Unfortunately, these prior processes have often involved long reaction times, expensive and dangerous reagents, relatively low yields, an inability to scale to production quantities of ferrocene, and other problems. Thus, an improved method of producing ferrocene is desirable, particularly one that may also be useful in preparing other cyclopentadiene-metal compounds in addition to ferrocene.

SUMMARY

The present invention solves these and other problems of the prior processes. According to the present invention, ferrocene is produced from a mixture of $FeCl_2$, cyclopentadiene anion, diethylamine, and dibenzo-18-crown-6-potassium complex, with further petroleum ether extraction of the prepared product. The present invention provides an economically viable process for continuous production of high purity ferrocene with good yields but without use of dangerous or expensive reagents or catalysts.

In accordance with the present invention, the dibenzo-18-crown-6-potassium interacts with diethylamine to produce a catalyst for the production of cyclopentadiene. The cyclopentadiene then reacts with the iron chloride and the diethylamine to produce ferrocene. The process can be made continuous, and has high yields. Furthermore, the process may be used to prepare other cyclopentadiene metal compounds, such as those of the metals titanium, zirconium, hafnium, vanadium, chromium, molybdenum, tungsten, manganese, ruthenium, osmium, cobalt, rhodium, and nickel.

DETAILED DESCRIPTION

According to the present invention, ferrocene is made using mixture of $FeCl_2$, cyclopentadiene, diethylamine, and a catalytic quantity of dibenzo-18-crown-6 complexed with potassium. After production, the ferrocene is purified by petroleum ether extraction. As presently understood, the process initially involves interaction of the dibenzo-18-crown-6 potassium (II) with diethylamine to form a potassium anion-diethylamin-dibenzo-18-crown-6-potassium-cation complex (III):

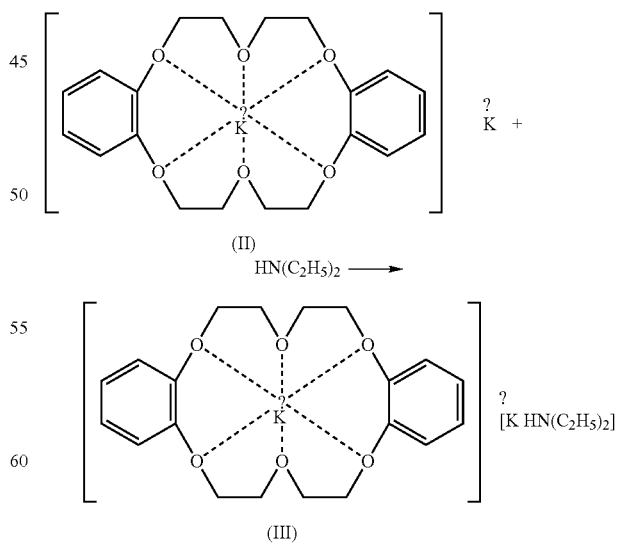

The resulting complex (III) then accepts a proton to form anionic cyclopentadiene (IV) in the mixture:

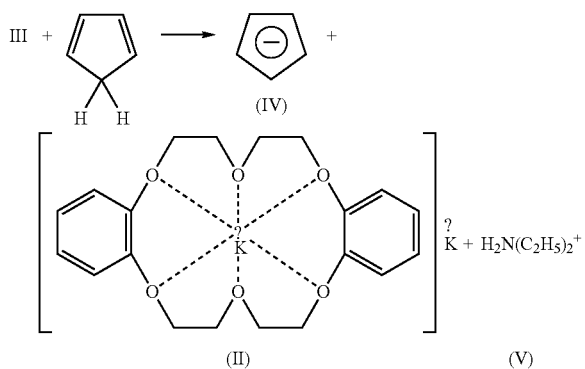

The anionic cyclopentadiene (IV) then reacts with the iron chloride and cationic diethylamine (V) to form ferrocene (I) and diethylamine chloride:

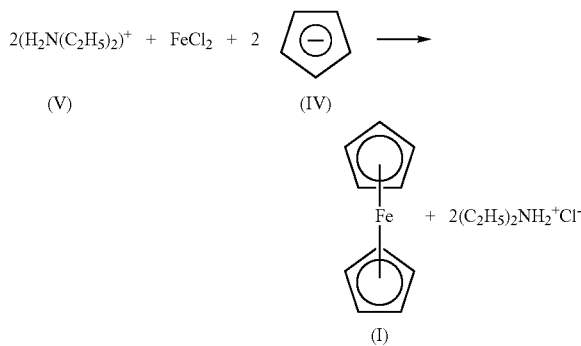

The catalytic action of the crown ether reduces the production time for ferrocene by 50% compared prior processes without the the need for expensive or dangerous reagents such as tetrahydrofuran and without other drawbacks of prior methods.

As shown, the catalysts are preferably complexes of crown ethers with alkali metals but cryptand-alkal metal complexes may also be used. At the present, the crown ether catalyst appears to work best at a concentration of 0.001–0.005% of the concentration of cyclopentadiene. Using crown ethers and cryptands as phase transfer catalysts, the method of the present invention may also be used to produce di-alkyl substituted ferrocenes of the structure:

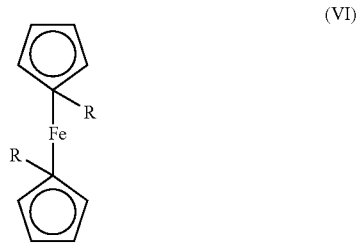

The method of the present invention may also be used to prepare other organometallic compounds of cyclopentadiene such as those of manganese, cobalt and chromium. Such metallocenes have the structure:

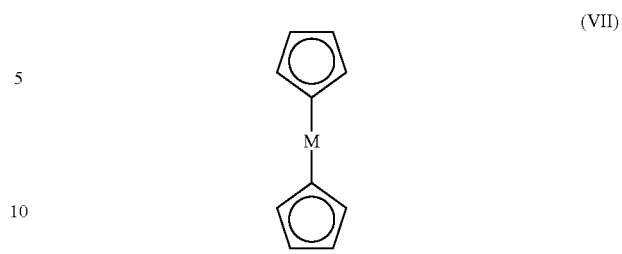

where M may be titanium, zirconium, hafnium, vanadium, chromium, molybdenum, tungsten, manganese, iron, ruthenium, osmium, cobalt, rhodium, or nickel.

EXAMPLES 31.7 g (0.25 mol) of dry iron chloride ($FeCl_2$) was added to a mixture of 42 ml (0.5 mol) cyclopentadiene, 100 ml of diethylamine, 3.9 mg (0.0001 mol) of potassium and 0.0360 (0.0001 mol) dibenzo-18-crown-6 ether in a cooled flask under a dry nitrogen atmosphere. The solution was mixed vigorously at room temperature for 4 hours. Surplus diethylamine was removed under a vacuum, returning approximately 40% of the initial diethylamine. The residue was extracted several times by boiling with petroleum ether in a flask equipped with a reverse cooler. The extract was filtered hot and, after removing the solvent, ferrocene (orange product having a melting point of 172–173?C) remained. The yield was 77–84%. The residue was treated with dry sodium hydroxide to recover the diethylamine in salt form ($[(C_2H_5)_2NH_2]Cl$), after which the residue was treated with hot water and the crown ether removed by vacuum distillation.

Table 1 shows the experimental results:

TABLE 1

Experimental Results of Ferrocene Preparation According to the Present Invention.

| Process Duration, hours | Developed method of preparation of ferrocene, % Mol relations of cyclopentadiene to $FeCl_2$ | | | |
| --- | --- | --- | --- | --- |
| | 1:2 | 1:1 | 2:1 | 3:1 |
| 0.5 | 17.6 | 21.5 | 36.5 | 36.4 |
| 1.0 | 31.6 | 32.4 | 40.5 | 40.4 |
| 1.5 | 36.2 | 37.4 | 45.4 | 44.9 |
| 4.0 | 38.9 | 41.7 | 57.6 | 57.3 |
| 6.0 | 47.9 | 52.6 | 84.4 | 84.1 |
| 7.0 | 48.7 | 57.4 | 77.9 | 78.1 |

As the table shows, the process of the present invention develops good yields after only six hours, significantly less than prior processes. Increasing the reaction time further increases the yield.

For comparison purposes, 31.7 g (0.25 mol) of dry iron chloride ($FeCl_2$) was added to a mixture of 42 ml (0.5 mol) cyclopentadiene, and 100 ml of diethylamine in a cooled flask under a dry nitrogen atmosphere. The solution was mixed vigorously at room temperature for 6 hours. Surplus diethylamine was removed under a vacuum, returning approximately 40% of the initial diethylamine. The residue was extracted several times by boiling with petroleum ether in a flask equipped with a reverse cooler. The extract was filtered hot and, after removing the solvent, ferrocene remained. However, despite the longer reaction time, the yield without the potassium-dibenzo-18-crown-6 complex was only 56–58%. In a second comparison, 15.85 g (0.125 mol) of dry iron chloride (FeCl2), 21 ml (0.25 mol) of cyclopentadiene and 50 ml of diethylamine were reacted in the same fashion, and 13.1 g of ferrocene extracted, thus showing a yield of 30%.

Thus, the present invention has several advantages over the prior art and over reactions that do not involve the catalyst. Although embodiments of the present invention have been described, various modifications and changes may be made by those skilled in the art without departing from the spirit and scope of the invention.

The invention claimed is:

1. A process for producing ferrocene comprising the steps of:
   preparing a solution of predetermined amounts of dry iron chloride, cyclopentadiene, diethylamine, potassium and dibenzo-18-crown-6 ether in a cooled container under a dry nitrogen atmosphere;
   vigorously mixing the solution at room temperature for a predetermined period of time;
   removing any diethylamine under a vacuum;
   extracting the residue by boiling with petroleum ether in a vessel equipped with a reverse cooler;
   filtering the hot extract; and
   removing any solvent.

2. A process for producing ferrocene comprising the steps of:
   vigorously mixing a solution of iron chloride, cyclopentadiene, diethylamine, potassium and dibenzo-18-crown-6 ether; and
   extracting ferrocene from the solution.

3. The process of claim 2 wherein the solution is mixed in a cooled flask under a dry nitrogen atmosphere.

4. The process of claim 2 wherein the solution is mixed at room temperature for a predetermined period of time.

5. The process of claim 2 further comprising the steps of:
   removing any diethylamine under a vacuum;
   extracting the residue by boiling with petroleum ether in a flask equipped with a reverse cooler;
   filtering the hot extract; and
   removing any solvent.

6. A method for producing a predetermined organometallic compounds of cyclopentadiene having the structure:

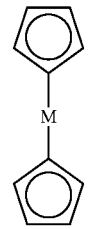

where M is a metal selected from the group consisting of titanium, zirconium, hafnium, vanadium, chromium, molybdenum, tungsten, manganese, iron, ruthenium, osmium, cobalt, rhodium, and nickel,
   the method comprising the steps of:
   vigorously mixing a solution of a selected salt of M, cyclopentadiene, diethylamine, potassium and dibenzo-18-crown-6 ether; and
   extracting the predetermined organometallic compound of cyclopentadiene from the solution.

7. The process of claim 6 wherein the solution is mixed in a cooled container under a dry nitrogen atmosphere.

8. The process of claim 6 wherein the solution is mixed at room temperature for a predetermined period of time.

9. The process of claim 6 further comprising the steps of:
   removing any diethylamine under a vacuum;
   extracting the residue by boiling with petroleum ether in a vessel equipped with a reverse cooler;
   filtering the hot extract; and
   removing any solvent.

* * * * *